(12) United States Patent
Carden et al.

(10) Patent No.: US 9,095,403 B2
(45) Date of Patent: Aug. 4, 2015

(54) DENTAL CERAMIC COLORING LIQUIDS

(71) Applicants: Robin A. Carden, San Juan Capistrano, CA (US); Frank A. Jimenez, Irvine, CA (US)

(72) Inventors: Robin A. Carden, San Juan Capistrano, CA (US); Frank A. Jimenez, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 158 days.

(21) Appl. No.: 13/651,401

(22) Filed: Oct. 13, 2012

(65) Prior Publication Data

US 2014/0101869 A1    Apr. 17, 2014

(51) Int. Cl.
| | |
|---|---|
| *C09K 3/00* | (2006.01) |
| *A61C 13/08* | (2006.01) |
| *A61K 6/00* | (2006.01) |
| *C04B 41/85* | (2006.01) |
| *C04B 41/00* | (2006.01) |
| *C04B 41/50* | (2006.01) |
| *A61K 6/02* | (2006.01) |
| *C04B 111/00* | (2006.01) |
| *C04B 111/82* | (2006.01) |

(52) U.S. Cl.
CPC .............. *A61C 13/082* (2013.01); *A61K 6/0005* (2013.01); *A61K 6/0094* (2013.01); *A61K 6/021* (2013.01); *A61K 6/0225* (2013.01); *C04B 41/009* (2013.01); *C04B 41/5007* (2013.01); *C04B 41/85* (2013.01); *C04B 2111/00112* (2013.01); *C04B 2111/82* (2013.01)

(58) Field of Classification Search
CPC ......... A61K 6/04; A61K 6/043; A61K 6/021; A61K 6/0225; A61C 13/082
USPC ............................................ 106/35
See application file for complete search history.

(56) References Cited

U.S. PATENT DOCUMENTS

| 4,557,691 | A | 12/1985 | Martin et al. | |
|---|---|---|---|---|
| 6,709,694 | B1 | 3/2004 | Suttor et al. | |
| 2002/0081269 | A1* | 6/2002 | Trom et al. | ............ 424/49 |
| 2008/0303181 | A1 | 12/2008 | Holand et al. | |
| 2009/0042167 | A1 | 2/2009 | Van Der Zel | |
| 2010/0062398 | A1 | 3/2010 | Schechner et al. | |
| 2010/0221683 | A1* | 9/2010 | Franke et al. | ............ 433/215 |
| 2011/0151411 | A1 | 6/2011 | Schechner et al. | |
| 2013/0231239 | A1 | 9/2013 | Carden et. al | |
| 2014/0109797 | A1 | 4/2014 | Carden | |
| 2014/0178834 | A1* | 6/2014 | Jahns et al. | ............ 433/141 |

FOREIGN PATENT DOCUMENTS

| DE | 196 19 165 | 9/1997 |
|---|---|---|
| EP | 2 025 659 | 2/2009 |
| EP | 2 505 163 | 10/2012 |
| WO | 2013070451 | 8/2013 |
| WO | 2013130553 | 9/2013 |

OTHER PUBLICATIONS

Extended European Search Report issued in European Application No. 13188299.5 dated Feb. 6, 2014.

* cited by examiner

*Primary Examiner* — Eisa Elhilo

(57) ABSTRACT

A coloring liquid especially for shading pre-sintered ceramic dental restorations, utilizes a combination of metal salt, solvent and acid to achieve natural tooth coloring of standard dental shades. By adjusting the respective ingredients, different shades can be provided and color penetration can be sufficient to preserve aesthetics in the sintered restoration even when some of the ceramic material is removed.

19 Claims, No Drawings

DENTAL CERAMIC COLORING LIQUIDS

A coloring liquid especially for shading pre-sintered ceramic dental restorations, utilizes a combination of metal salt, solvent and acid to achieve natural tooth coloring of standard dental shades. By adjusting the respective ingredients, different shades can be provided and color penetration can be sufficient to preserve aesthetics in the sintered restoration even when some of the ceramic material is removed.

BACKGROUND OF THE INVENTION

1. Field of the Invention

The present invention relates to a ceramic dental restoration coloring solution that contains an organic solvent. The purpose for this solvent is to assure the homogeneity of the solution that contains metallic salts. Derivatives of propylene oxide can be used for this purpose. The coloring solution should comprise an organic solvent of 1% to about 5% by weight.

The present invention also relates to a dental restoration coloring solution that contains acid. The more acidic is the solution, the deeper the color penetration will result. Adding an acid will decrease the pH further, prompting an increase in color penetration. An acidic pH level in the range of 1.0 to 3.0 is preferred.

2. Background Discussion

Aesthetics are a very significant factor when evaluating dental restorations. In particular, the translucency and color of a restoration are especially important. When considering ceramic dental restorations, the translucency is an innate optical property of the material. However, the color needs to be added to the ceramic. At present, a coloring solution containing metallic salts is used to color a pre-sintered ceramic body.

When applying color to a ceramic dental restoration, a specific hue, value, and chroma must be present to match the aesthetics of a natural tooth. Therefore, specific metallic salts are chosen to match these colors. Furthermore, the penetration of the coloring solution of the ceramic should be maximized to allow for adjustments to be made on the restoration after final sinter. Should the color solution not penetrate deeply enough into the restoration, any grinding on the surface remove the colored ceramic and reveal the underlying white ceramic.

It should therefore be in the nature of the coloring solutions to produce the particular colors of natural teeth and to sufficiently penetrate the ceramic body. The present invention relates to a coloring solution containing specific metallic salts that not only produce these colors, but also has a chemical disposition to infiltrate the ceramic body thereby ensuring that the color sufficiently penetrates the dental restoration.

SUMMARY OF THE INVENTION

The present invention relates to a coloring solution for ceramic dental restorations that consist of metallic salts, a pH adjusting agent, and a solvent to disperse the salts into solution.

An object of this invention is to create a coloring solution that can create colors of a specific hue, chroma, and value when applied to a ceramic body.

A further object is to create a coloring solution that will infiltrate a ceramic body such that the color penetrates the ceramic body to a depth of at least 1 mm.

Still a further object is to use specific metallic salts and other components that will yield the desired colors and penetration depths.

A coloring solution comprising a metallic salt, a solvent, an organic solvent such as derivatives of propylene oxides, and an acid are mixed together to create a coloring agent for pre-sintered ceramic bodies.

DETAILED DESCRIPTION OF PREFERRED EMBODIMENTS

The present invention utilizes metallic salts as the coloring agent present in the coloring liquid. The primary properties of the salt are such that it is soluble in solvent, produces the desired colors after the ceramic body is sintered, and is chemically able to penetrate into the body. Metallic salts of transition metals from groups 3-12 on the periodic table can be used for the coloring solution. In addition, salts from rare earth metals can be used as well. Metallic salts in the forms of oxides or containing anions such as: $Cl^-$, $SO_4^-$, $SO_3^-$, $Br^-$, $F^-$, $NO_2^-$, and $NO_3^-$ may be used.

In particular, salts of the metallic ions terbium, chromium, and manganese are well suited to produce the necessary colors needed to achieve the natural aesthetics of human teeth.

When used to color a pre-sintered ceramic body, terbium yields a yellow hue, manganese a gray hue, and chromium a red-brown hue. A combination of these colors, directly dependent on the ratio of the chemicals used, will give the desired colors to a ceramic body.

Preferably, terbium (III) chloride, chromium (III) chloride, and manganese (II) sulfate can be used. Due to the need of having soluble compounds in solution, it is desirable that these salts be hydrated. That is, they are in the form of complex metallic ions that can easily disassociate when in solution. Therefore, it is preferable to use terbium (III) chloride hexahydrate, chromium (III) chloride hexahydrate, and manganese (II) sulfate monohydrate.

The coloring solution should contain metallic salts in the range of 0.0001% to 1.0% by weight. The concentration of the metallic salts is directly dependent on the target color that is to be achieved.

An advantage of using these metallic salts not only stems from the colors they yield, but also the manner in which they react with the solvent. The primary property of the solvent is such that it can dissolve the metallic salts and facilitate a homogenous solution. Solvents can include water, alcohols, ketones, organic solvents, or mixtures thereof. The solvent comprises the majority of the solution by weight. As it relates to the present invention, the preferred solvent is de-ionized water.

Using hydrates of the metallic salts facilitates solubility, thereby assuring that the compounds disassociate into their respective ionic species. This promotes the hydrolysis of the metallic ions once in solution. Hydrated metallic ions behave as weak acids in aqueous solution.

The propensity of these salts to act as weak acids serves a unique function for this invention. By acting as an acid, the hydrated metal ions lower the solution pH. Solutions with low pH values in turn have a tendency to infiltrate the ceramic body more so than a solution with a higher pH. The driving force behind higher infiltration and deeper color penetration is an acidic solution. Therefore, by using the selected metallic salts, a naturally acidic solution is created. Furthermore, color penetration is promoted due to the lower pH.

The present invention relates to a ceramic dental restoration coloring solution that also contains an organic solvent. The purpose for this solvent is to assure the homogeneity of the solution that contains the metallic salts. Derivatives of propylene oxide can be used for this purpose.

The coloring solution should comprise an organic solvent of 1% to about 5% by weight.

The present invention relates to a coloring solution that also contains acid. As stated previously, the more acidic the solution, the deeper color penetration will result. Adding an acid will decrease the pH further, prompting an increase in color penetration. An acidic pH level in the range of 1.0 to 3.0 is preferred.

Using hydrochloric acid as the pH adjusting agent is ideal where the solution already contains chlorides. Because the Cl⁻ anion will not hydrolyze, no effect on pH will occur. This is a benefit of using metal chlorides. Although the chloride anion itself is neutral, it does not adversely affect the pH of the solution, thereby allowing the hydrolysis of the metal cations, in this case $Tb^{3+}$, $Mn^{2+}$, and $Cr^{3+}$, to occur. This of course leads to the acidification of the coloring solution, which gives the coloring liquid the driving force behind deeper color penetration.

The present invention relates to a coloring liquid comprising metallic salts, a solvent, and a pH adjusting agent. Such a mixture ensures homogenous coloring of a ceramic body to match the colors of a natural tooth.

By selecting metallic salts that will cause an acidic shift in solution, deeper color penetration is ensured. The addition of an acid perpetuates color infiltration. The use of hydrochloric acid adds a similar species of ions to the solution and ensures no additional chemical reactions occur that could alter the chemical makeup of the solution.

Application

The present invention can be applied to the coloring of ceramic materials, particularly those used in the dental industry for dental restorations. Pre-sintered ceramic crowns and bridges can be colored using the coloring liquid to match the aesthetics of natural teeth.

At present, dental frameworks are milled from zirconia blocks. Because the natural color of zirconia is white, there is a need to color the ceramic. Current methods involve the immersion of a pre-sintered zirconia framework of final shape into the color liquid for a specified soaking time period. Frameworks are subsequently dried and sintered. The dental industry at large uses the VITA Classic shade guide as a standard for teeth aesthetics. These colors are unique in hue, chroma, and value. The present invention relates to color liquids that are made to match these properties.

Testing Results:

Successful results have been achieved with the present invention.

First Test

A coloring solution containing $TbCl_3$, $CrCl_3$, propylene glycol, 37% hydrochloric acid, and deionized water was mixed to form a coloring liquid that produce the VITA Classic Shades.

The exact composition of the coloring solution is as follows: 0.0530 wt % $TbCl_3 \cdot 6H_2O$, 0.0471 wt % $CrCl_3 \cdot 6H_2O$, 2.033 wt % propylene glycol, and 0.10 wt % hydrochloric acid. The balance was deionized water. The final pH of the solution was measured to be 1.92.

Zirconia restorations were colored using this coloring liquid and were followed by a sintering process. After final sinter, the colored ceramic was cut to assure adequate color penetration.

Total and homogenous coloring of the ceramic restoration was achieved. Using a VITA Easyshade instrument, the color was checked to verify if a dental shade had indeed been matched. The final color matched closely to the VITA Classic shade A2.

Second Test

A second test was performed to verify the results of the first. A coloring liquid of different composition and concentration was used for processing.

The exact composition of the coloring solution is as follows: 0.0613 wt % $TbCl_3 \cdot 6H_2O$, 0.0072 wt % $MnSO_4 \cdot H_2O$, 0.0221 wt % $CrCl_3 \cdot 6H_2O$, 2.033 wt % propylene glycol, and 0.10 wt % hydrochloric acid. The balance was deionized water. The final pH of the solution was measured to be 1.93.

Zirconia restorations were colored using this coloring liquid and were followed by a sintering process. After final sinter, the colored ceramic was cut to assure adequate color penetration.

Total and homogenous coloring of the ceramic restoration was achieved. Using a VITA Easyshade instrument, the color was checked to verify that a dental shade had indeed been matched. The final color matched closely to the VITA Classic shade B1.

Third Test

A third test was performed to verify the results of the first two. A coloring liquid of different composition and concentration was used for processing.

The exact composition of the coloring solution is as follows; 0.0935 wt % $TbCl_3 \cdot 6H_2O$, 0.0624 wt % $CrCl_3 \cdot 6H_2O$, 2.033 wt % propylene glycol, and 0.10 wt % hydrochloric acid. The balance was deionized water. The final pH of the solution was measured to be 1.93.

Zirconia restorations were colored using this coloring liquid and were followed by a sintering process. After final sinter, the colored ceramic was cut to assure adequate color penetration.

Total and homogenous coloring of the ceramic restoration was achieved. Using a VITA Easyshade instrument, the color was checked to verify that a dental shade had indeed been matched. The final color matched closely to the VITA Classic shade A3.

Therefore, the present invention, as it relates to a coloring liquid comprises metallic salts and an acid that promote colors that match the aesthetics of natural teeth and color penetration. This coloring liquid has proven to be useful in the dental industry to create a dental ceramic with intrinsic colors that match the desired aesthetics of dental frameworks.

What is claimed is:

1. A coloring liquid for shading ceramic dental restorations to match natural teeth, the liquid comprising an organic solvent, an acid, and at least one metallic salt, wherein the amount of metallic salt in the liquid comprises 0.0001% by weight to 1.0% by weight of the liquid, wherein the at least one metallic salt comprises a rare earth metal, and wherein the acid comprises hydrochloric acid.

2. The coloring liquid recited in claim 1 wherein said metallic salt comprises at least one salt having metallic ions from the group consisting of terbium, chromium and manganese.

3. The coloring liquid recited in claim 1 wherein said metallic salt comprises at least one of salts having anions from the group consisting of $Cl^-$, $SO_4^{2-}$, $SO_3^-$, $Br^-$, $F^-$, $NO_2^-$, and $NO_3^-$.

4. The coloring liquid recited in claim 1 wherein said metallic salt is hydrated.

5. The coloring liquid recited in claim 2 wherein the metallic salt is hydrated and comprises at least one of terbium (III) chloride, chromium (III) chloride and manganese (II) sulfates.

6. The coloring liquid recited in claim 1 wherein said metallic salt comprises at least one of terbium (III) chloride hexahydrate, chromium (III) chloride hexahydrate, and manganese (II) sulfate monohydrate.

7. The coloring liquid recited in claim 1 having an organic solvent of 1% to about 5% by weight of said liquid.

8. The coloring liquid recited in claim 1 wherein said acid produces a pH level of 1.0 to 3.0 for said liquid.

9. The coloring liquid recited in claim 1 wherein said organic solvent comprises propylene glycol.

10. The coloring liquid recited in claim 6 wherein said liquid comprises terbium (III) chloride hexahydrate in the range of 0.0530 wt % to 0.0935 wt %.

11. A coloring liquid for shading ceramic dental restorations to match the color of natural teeth, the liquid comprises metallic salts consisting of $TbCl_3$, $CrCl_3$ and $MnSO_4$;
an acid;
an organic solvent; and
water,
wherein the amount of metallic salt in the liquid is in the range of 0.0001% by
weight to 1.0% by weight, and wherein the acid comprises hydrochloric acid.

12. A coloring liquid comprising an organic solvent, an acid, and at least one metallic salt as a coloring agent, wherein the amount of metallic salt in the liquid is in the range of 0.0001% by weight to 1.0% by weight of the liquid, and wherein said acid comprises hydrochloric acid.

13. The coloring liquid recited in claim 11 wherein said organic solvent comprises propylene glycol.

14. The coloring liquid recited in claim 11 wherein said acid is selected to produce a coloring liquid having a pH of between 1.0 and 3.0.

15. The coloring liquid recited in claim 11 wherein said solution comprises $TbCl_3$ in the range of 0.05 wt % to 0.09 wt %.

16. The coloring liquid of claim 1, wherein the metallic salt of a rare earth metal is a salt of the metallic ion terbium.

17. The coloring liquid of claim 1, wherein the coloring liquid comprises about 0.05 wt % to about 0.09 wt % of a metallic salt having terbium ions.

18. The coloring liquid of claim 12, comprising at least one metallic salt having metallic ions selected from terbium, chromium and manganese.

19. The coloring liquid of claim 12 wherein the liquid comprises terbium (III) chloride hexahydrate in the range of 0.0530 wt % to 0.0935 wt %.

* * * * *